US006605708B1

(12) United States Patent
Habus et al.

(10) Patent No.: US 6,605,708 B1
(45) Date of Patent: Aug. 12, 2003

(54) BUILDING BLOCKS WITH CARBAMATE INTERNUCLEOSIDE LINKAGES AND OLIGONUCLEOTIDES DERIVED THEREFROM

(75) Inventors: Ivan Habus, Shrewsbury, MA (US); Sudhir Agrawal, Shrewsbury, MA (US)

(73) Assignee: Hybridon, Inc., Cambridge, MA (US)

( * ) Notice: Subject to any disclaimer, the term of this patent is extended or adjusted under 35 U.S.C. 154(b) by 0 days.

(21) Appl. No.: 08/098,945

(22) Filed: Jul. 28, 1993

(51) Int. Cl.⁷ .............................................. C07H 21/00
(52) U.S. Cl. ..................... 536/23.1; 536/24.5; 536/25.3; 514/44
(58) Field of Search ............................. 536/23.1, 24.5, 536/25.3; 514/44

(56) References Cited

U.S. PATENT DOCUMENTS 5,149,797 A 9/1992 Pederson et al. .......... 536/24.5

FOREIGN PATENT DOCUMENTS

| EP | 0464638 | | 1/1992 |
| WO | 9106629 | * | 5/1991 |
| WO | WO 9220822 | | 11/1992 |
| WO | WO 9220823 | | 11/1992 |

OTHER PUBLICATIONS

Agrawal, "Antisense Oligonucleotides as Antiviral Agents," *Trends in Biotechnology*, 10, 152–158 (May, 1992).*
R. S. Root–Bernstein (I), "AIDS IS More Than HIV: Part I," *Genetic Engineering News*, Sep. 1, 1992, pp. 4–6.*
R. S. Root–Bernstein (II), "AIDS IS More Than HIV: Part II," *Genetic Engineering News*, Sep. 15, 1992, pp. 4–5.*
T. Beardsley, "Trends in Cancer Epidemiology—A War Not Won," *Scientific American*, 270(1), 130–138 (Jan., 1994).*
G. Zon, "Oligonucleotide Analogues as Potential Chemotherapeutic Agents," *Pharmaceutical Research*, 5(9), 539–549 (1988).*
Gait et al., *J. Chem. Soc., Perkin I*, 1684–1686 (1974).
Mungall and Kaiser, *J. Org. Chem.* 42, 703–706 (1977).
Coull et al., *Tetrahedron Lett.* 28, 745–748 (1987).
Stirchak et al., *Nucleic Acids Res.* 17, 6129–6141 (1989).
Wang and Weller, *Tetrahedron Lett.* 32, 7385–7388 (1991).
Damha et al., *Nucleic Acids Res.* 18, 3813 (1990).
Caruthers et al., *Methods in Enzymology* 154, 287 (1987).
Stirchak et al., *J. Org. Chem.* 52, 4202 (1987).
Weller et al., *J. Org. Chem.* 56, 6000 (1991).
Nyilas et al., *Tetrahedron* 46, 2149 (1990).

* cited by examiner

*Primary Examiner*—James O. Wilson
*Assistant Examiner*—L. Eric Crane
(74) *Attorney, Agent, or Firm*—Hale and Dorr LLP (57) ABSTRACT

The invention provides synthons containing a novel carbamate internucleoside linkage, methods for using such synthons to make oligonucleotides containing such novel carbamate linkages, and oligonucleotides containing such novel carbamate linkages.

13 Claims, 4 Drawing Sheets

BUILDING BLOCKS WITH CARBAMATE INTERNUCLEOSIDE LINKAGES AND OLIGONUCLEOTIDES DERIVED THEREFROM

BACKGROUND OF THE INVENTION

1. Field of the Invention

The invention relates to synthetic oligonucleotides. More particularly, the invention relates to synthetic oligonucleotides having modified internucleoside linkages that confer resistance to nucleolytic degradation.

2. Summary of the Related Art

In recent years there has been considerable interest in the use of synthetic oligonucleotides as modulators of gene expression. (See, for example, Agrawal, Trends in Biotechnology 10:152–158 (1992)). At least part of this interest has been directed toward the development of modified oligonucleotides having greater resistance to nucleolytic degradation than is possessed by conventional oligonucleotide phosphodiesters. Included among such oligonucleotides are chimeric oligonucleotides having different types of modified internucleotide linkages. For example, Pederson et al., U.S. Pat. No. 5,149,797, discloses chimeric oligonucleotides having regions that activate RNase H and regions that do not activate RNase H.

Among the modified internucleoside linkages that have been incorporated into oligonucleotides are phosphate-based and non-phosphate-based linkages. The former group includes the well known phosphorothioate, phosphorodithioate, methylphosphonate and phosphoramidate linkages, among others. The latter group includes sulfone, sulfate and carbamate linkages. Such linkages modify oligonucleotides in a manner that can affect the oligonucleotide in its abilities to resist nucleolytic degradation, undergo normal hydrogen bonding and base stacking, bind to a complementary target nucleic acid, and be taken up by cells.

Certain types of carbamate internucleoside linkages are known in the art. Gait et al., J. Chem. Soc., Perkin I:1684–1686 (1974) first disclosed a dinucleotide containing a carbamate internucleotide linkage of the structure 5'-nucleoside-3'-OCONH-5'-nucleoside-3'. Mungall and Kaiser, J. Org. Chem. 42:703–706 (1977), discloses synthesis of modified dinucleotides and trinucleotides having carbamate linkages of the same structure. Coull et al., Tetrahedron Lett. 28:745–748 (1987), teaches that a hexameric oligonucleotide carbamate having the same internucleoside linkage does not undergo base stacking, even though its size and shape should not produce steric hindrance. Stirchak et al., Nucleic Acids Res. 17:6129–6141 (1989), discloses that a hexameric poly C morpholine oligonucleotide carbamate having the same internucleoside linkage forms a multistrand complex, rather than a Watson-Crick duplex, with complementary poly (dG). Wang and Weller, Tetrahedron Lett. 32:7385–7388 (1991) disclose solid phase synthesis of oligonucleotide or morpholine oligonucleotide carbamates having this same internucleotide linkage.

Although oligonucleotide carbamates are of interest for use as modulators of gene expression due to their stability over a wide pH range and their resistance to enzymatic degradation, the absence of base stacking and the formation of multi-strand complexes by unknown mechanisms may hinder such a use as a practical matter. Consequently, there is a need for new linkages having similar resistance to degradation, but without hindering the ability of oligonucleotides to undergo base stacking and, at least in some configurations, without significantly destabilizing the double helix formed between the oligonucleotide and its complementary target nucleic acid.

BRIEF SUMMARY OF THE INVENTION

The invention provides convenient building blocks for assembling oligonucleotides containing a novel carbamate linkage. The carbamate linkage in building blocks and oligonucleotides according to the invention has the structure 5'-nucleoside-3'-NHCOO-5'-nucleoside-3', which is the reverse of the structure of known carbamate internucleoside linkages. Surprisingly, oligonucleotides containing this novel carbamate linkage do undergo base stacking, unlike known carbamate-linked oligonucleotides. In addition, the stability of double helices involving oligonucleotides according to the invention is not significantly impaired when the novel carbamate linkages are present in certain preferred positions within the oligonucleotides.

In a first aspect, the invention provides dimeric, trimeric and tetrameric building blocks in which at least two nucleosides are linked by the novel carbamate linkage 5'-nucleoside-3'-NHCOO-5'-nucleoside-3'. Such building blocks preferably have appropriate protecting or leaving groups for oligonucleotide synthesis at their 5' and 3' ends. These building blocks can be easily made using solution phase chemistry, and can be used for oligonucleotide assembly just like the protected monomers currently used.for solid phase oligonucleotide synthesis. Such building blocks according to the invention are useful for assembling oligonucleotides having novel carbamate internucleoside linkages at various positions within the oligonucleotide.

In a second aspect, the invention provides a method of using building blocks according to the invention to assemble oligonucleotides containing novel carbamate linkages. In this aspect, conventional oligonucleotide synthesis chemistries are utilized with the building blocks according to the invention.

In a third aspect, the invention provides novel oligonucleotides containing the carbamate internucleoside linkage 5'-nucleoside-3'-NHCOO-5'-nucleoside-3' at one or more positions within the oligonucleotide. Such oligonucleotides are readily assembled using conventional solid phase chemistry, but using dimeric, trimeric, or tetrameric building blocks according to the invention during one or more cycles of assembly. Such oligonucleotides according to certain embodiments of the invention are useful for studying the position-dependence of the effect of carbamate internucleoside linkages on destabilizing a double helix. In certain preferred embodiments of oligonucleotides according to the invention, the novel carbamate linkages are in positions that do not result in significant destabilization of a double helix formed between the oligonucleotide and a complementary target nucleic acid. Most preferably, such novel carbamate linkages are in positions in which they confer upon the oligonucleotide increased resistance to nucleolytic degradation. Oligonucleotides according to such an embodiment are useful for modulating gene expression, both in in vitro experimental systems and in therapeutic uses for plant, animal or human diseases.

DETAILED DESCRIPTION OF THE PREFERRED EMBODIMENTS

The invention relates to synthetic oligonucleotides having modified internucleoside linkages that confer resistance to nucleolytic degradation. The invention provides building blocks containing a novel carbamate internucleoside linkage, a method of using such building blocks to assemble oligonucleotides, and oligonucleotides containing novel carbamate internucleoside linkages.

Figure 1:
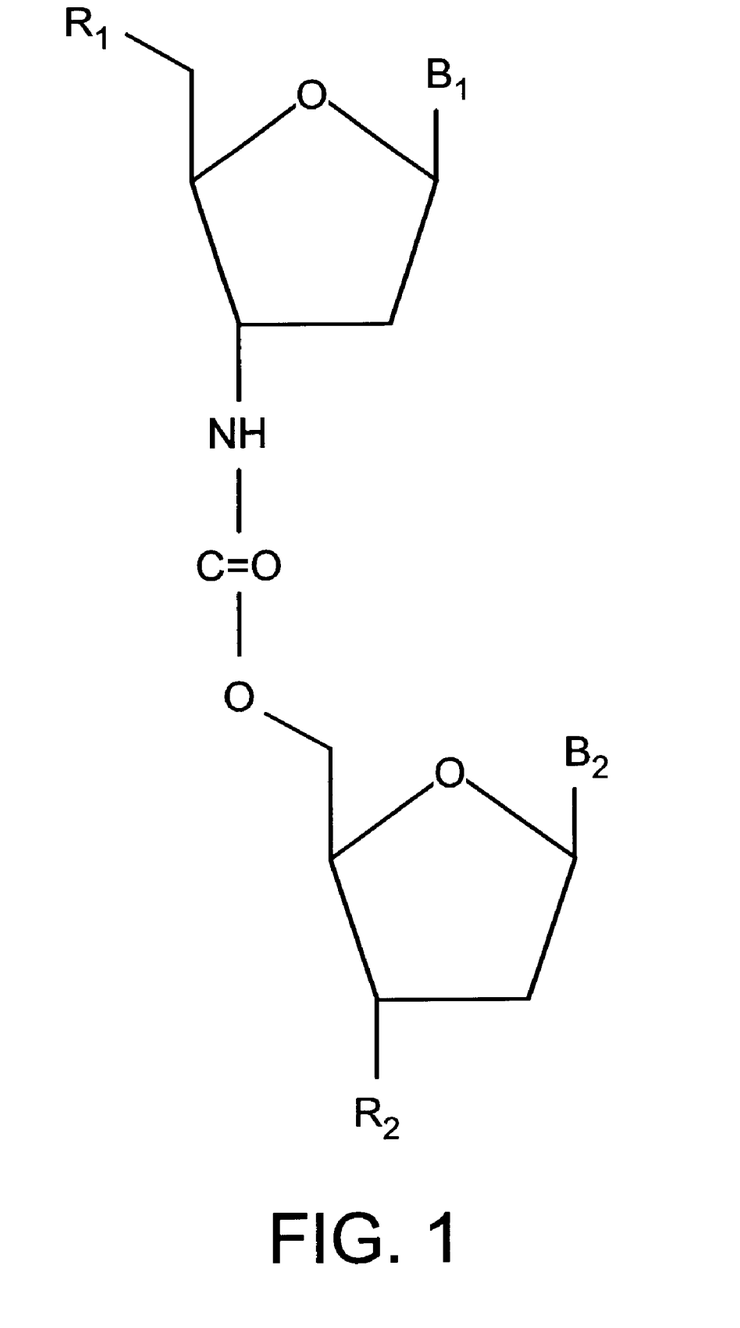
FIG. 1 shows the general structure of a dimeric building block according to the invention. Trimeric and tetrameric building blocks have similar structure.

In a first aspect, the invention provides convenient building blocks for assembling oligonucleotides containing a novel carbamate internucleoside linkage. Building blocks according to the invention have two, three, or four nucleosides that are connected by a novel carbamate internucleoside linkage having the structure 5'-nucleoside-3'-NHCOO-5'-nucleoside-3', which is the reverse of known carbamate internucleoside linkages. The general structure of an embodiment of a dimeric building block according to the invention is shown in FIG. 1. For the sake of simplicity in the number of compounds being exemplified, only building blocks having 5' thymidine nucleosides were constructed in the examples below. However, the base of the 5' or 3' nucleoside can be any purine or pyrimidine, or any analog thereof that is capable of engaging in base-pairing in a Watson-Crick double helix or Hoogsteen triple helix. The nucleosides may be ribonucleosides or deoxyribonucleosides. As shown in FIG. 1, $R_1$ or $R_2$ is preferably a hydroxyl group, an acid labile protective group such as dimethoxytrityl, a base labile protective group such as levulinyl or a leaving group such as a phosphotriester, H-phosphonate or phosphoramidite group, most preferably a beta-cyanoethylphosphoramidite group. Most preferably, the combinations of $R_1$ and $R_2$ within a particular building block are selected from those shown in Table I, below.

TABLE I

PREFERRED STRUCTURE OF BUILDING BLOCKS

| When $R^1$ is: | Then preferably $R^2$ is: |
|---|---|
| DMT | hydroxyl, levulinyl, phosphoramidite, H-phosphonate or phosphotriester |
| hydroxyl | hydroxyl or DMT |
| levulinyl or phosphoramidite | DMT |
| esterified to CPG | phosphoramidite, H-phosphonate or phosphotriester |

Trimeric and tetrameric building blocks according to the invention have essentially the same structure as described above for dimeric building blocks.

The synthesis of building blocks according to the invention is typically achieved by reaction of mono-, di-, or trimeric nucleoside 5'-O-p-nitrophenyl carbonate intermediates with 3'-amino-3'-deoxythimidine (or 3'-amino-3'-deoxyuridine), with the reaction occurring regio-specifically at the 3'-amine. The building blocks thus obtained are then protected at the 5'-position with dimethyoxytrityl (DMT), followed by hydrolysis of the 3'-acetyl in ammonia to provide a 3'-hydroxyl group. The building blocks are then converted into corresponding 3'-phosphoramidites by standard procedures.

In the synthesis procedures described herein, organic chemicals used in organic synthesis, HPLC-grade and anhydrous solvents were obtained from Aldrich and Fisher Scientific Co., and used as received. 3H-1,2-Benzodithiole-3-one-1,1-dioxide, was purchased from R.I. Chemical Inc., and used as a solution of 1 g in 100 ml of acetonitrile. TLC was performed on Merck's DC alufolien with Kieselgehl 60F-254, and column chromatography on silica gel, (Silica gel 60, 230–400 mesh ASTM, Merck). Illustrations of such synthesis procedures in greater detail of description are provided in Example 1, below.

In a second aspect, the invention provides a method of using building blocks according to the invention to assemble oligonucleotides containing one or more novel carbamate linkage(s). In one example of this method of use, building blocks are directly covalently bonded to a suitable solid phase support matrix. In one preferred embodiment, the support matrix is long chain alkylamidopropanoic acid controlled pore glass (CPG) and the carboxyl moiety is esterified directly with the 3' hydroxyl group of the building block. In this embodiment, one to three novel carbamate linkages are introduced at the most 3' internucleoside position in the synthesized oligonucleotide. Depending upon the nature of the oligonucleotide to be synthesized, additional novel carbamate internucleotide linkages can be introduced in groups of one to three at other positions within the oligonucleotide by using building blocks according to the invention. Additionally or alternatively, phosphodiester, phosphorothioate, phosphorodithioate, alkylphosphonate, alkylphosphonothioate, phosphoramidate, or any other well known internucleoside linkage can be introduced in any other position within the molecule using well known solid phase chemistry approaches. In alternative embodiments, building blocks according to the invention can be used to introduce novel carbamate linkages into an oligonucleotide at various positions without introducing such linkages at the most 3' internucleoside positions. This is accomplished by not attaching the building blocks directly to the solid support matrix, but rather to the growing nascent oligonucleotide chain, which has been initiated using other types of building blocks, such as nucleoside phosphoramidite monomers.

Generally, the method of using building blocks according to the invention to assemble oligonucleotides containing novel carbamate internucleoside linkages is carried out using well-known, conventional synthetic chemistries except for the use of the di-, tri-, or tetrameric building blocks. The phosphoramidite approach is most preferred and is exemplified herein. However, other known approaches may be used, such as the H-phosphonate approach disclosed in U.S. Pat. No. 5,149,798, the teachings of which are incorporated herein by reference. Even the venerable phosphotriester approach can be used with the building blocks according to the invention. In these cases, building blocks according to the invention are derivatized to form the corresponding di-, tri-, or tetranucleotide H-phosphonate or phosphotriester using the same well-known chemistries that are currently used to derivatize nucleoside monomers to form the corresponding nucleoside H-phosphonate or phosphotriester. The building blocks are then used to assemble oligonucleotides in the known H-phosphonate or phosphotriester procedures.

In a third aspect, the invention provides synthetic oligonucleotides containing novel carbamate internucleoside linkages at one or more internucleoside positions within the oligonucleotide. Such oligonucleotides are preferably from about 8 to about 100 nucleotides in length. The nucleotides may be ribonucleotides or deoxyribonucleotides. For any given oligonucleotide the maximum number of novel carbamate internucleoside linkages that can be present can be readily calculated by the equation n=3x, where n is the number of novel carbamate linkages present in the oligonucleotide and x is the number of building blocks used to assemble the oligonucleotide. Thus, for a 100-mer, the maximum number of novel carbamate internucleoside linkages is seventy-five, based upon assembly using twenty-five tetrameric building blocks according to the invention.

In a preferred embodiment, oligonucleotides according to the invention have novel carbamate linkages only at their most 3' internucleoside positions. Most preferably, such oligonucleotides will have novel carbamate linkages at only their first, second and/or third most 3' internucleoside positions. Oligonucleotides according to this embodiment are more resistant to nucleolytic degradation than conventional oligonucleotides, and are capable of participating in hydrogen bonding, base stacking and duplex formation. Accordingly, oligonucleotides according to this embodiment are useful as antisense or antigene agents when they have a nucleotide sequence that hybridizes under physiological conditions with a nucleic acid from a virus, prokaryotic or eukaryotic pathogen, or a cellular gene or gene expression controlling region. In a most preferred embodiment, such oligonucleotides contain additional modified internucleoside linkages that further increase the nuclease resistance of the oligonucleotide without interfering with its ability to participate in duplex formation. Such internucleoside linkages may be chosen from any of the well-known modified linkages, preferably from phosphorothioate, phosphorodithioate, alkylphosphonate, alkylphosphonothioate, or phosphoramidate linkages or any combination of these, and most preferably will be phosphorothioate internucleoside linkages.

The following examples are intended to further illustrate certain preferred embodiments of the invention and are not intended to be limiting in nature.

EXAMPLE 1

Synthesis of Dimeric, Trimeric, or Tetrameric Building Blocks Containing Exclusively as Internucleoside Linkages the Novel Carbamate Linkage 5'-Nucleoside-3'-NHCOO-5'-Nucleoside-3'

Synthesis of 3'-amino-3'-deoxythymidine was accomplished according to the standard hydrogenation procedure using 3'-azido-3'-deoxythymidine with Pd/C-10% Pd as catalyst and methanol as solvent. p-Nitrophenyl 3'-O-acetyl-deoxythymidine 5'-carbonate was prepared according to well-known procedures (See, e.g., Stirchak and Summerton, J. Org. Chem. 52:4202 (1987); Mungell and Kaiser, J. Org. Chem. 42:703 (1977)) in a reaction of 3'-O-acetyl-deoxythymidine with bis(p-nitrophenyl)carbonate.

Figure 2:
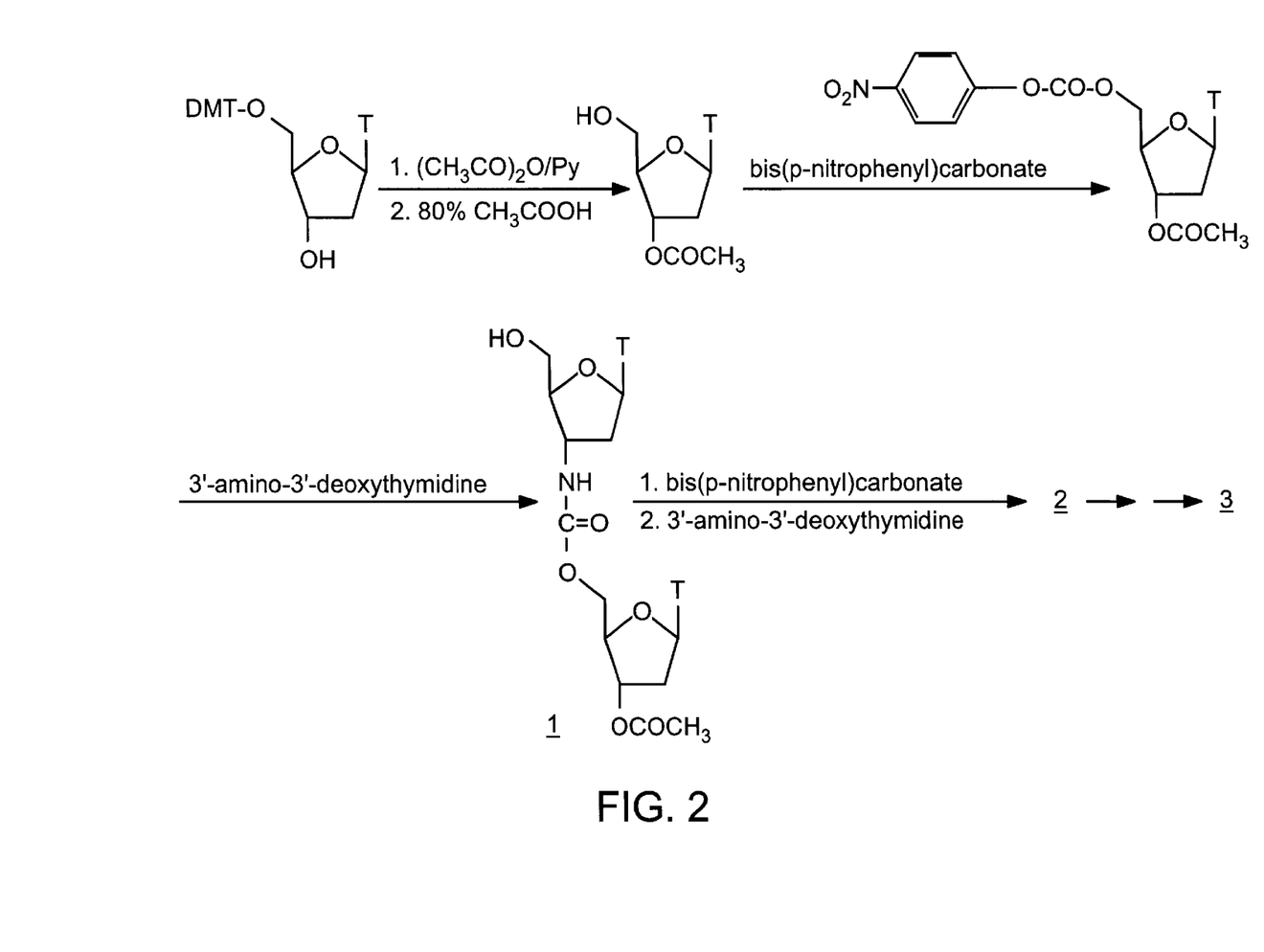
FIG. 2 illustrates the general scheme for synthesis of a dinucleoside carbamate building block according to the invention.
Figure 3:
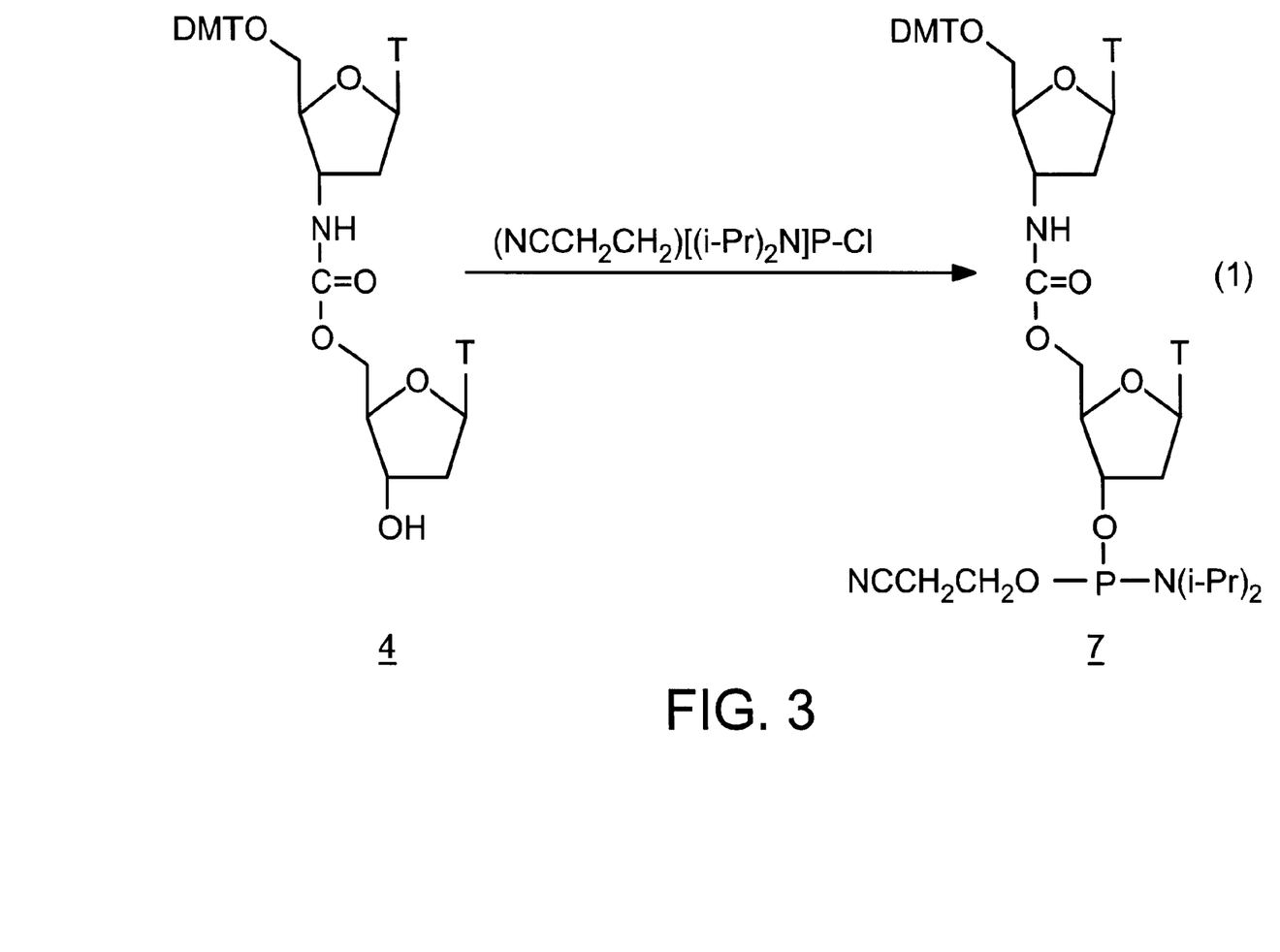
FIG. 3 illustrates the conversion of a dinucleoside carbamate building block into its phosphoramidite derivative.
Figure 4:
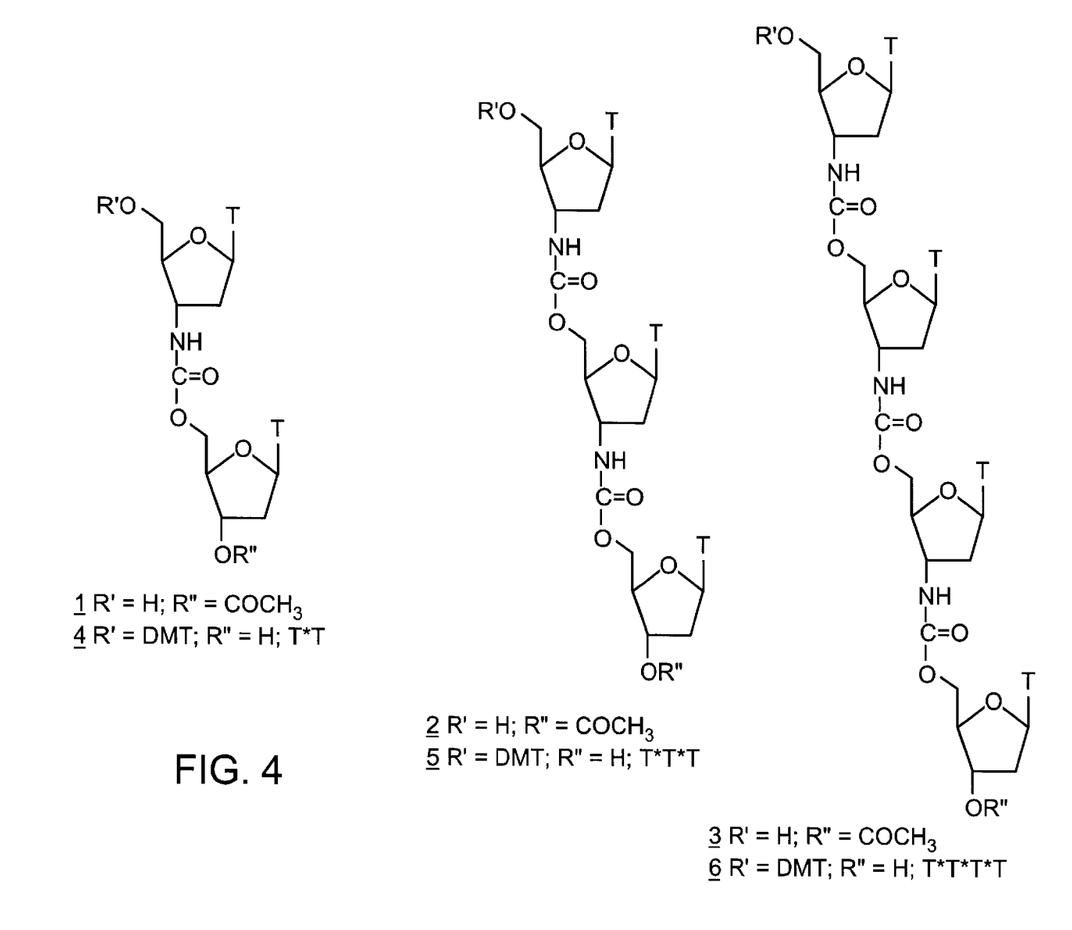
FIG. 4 shows examples of dinucleoside, trinucleoside and tetranucleoside carbamate intermediates and building blocks. Numbers under each compound correspond to the numbers given for each compound in Example 1.

First, 3'-amino-3'-deoxythymidylyl-(3'-5'-carbamoyl)-3'-O-acetyl-deoxythymidine, 1, was synthesized. The general scheme for this synthesis is shown in FIG. 2. p-Nitrophenyl 3'-O-acetyl-deoxythymidine 5'-carbonate, (324.68 mg; 0.72 mmole) and 3'-amino-3'-deoxythymidine (122.87 mg; 0.50 mmole) were dissolved in 5 ml of anhydrous pyridine at room temperature. The reaction mixture was stirred overnight under a nitrogen atmosphere. Solvent was then removed under reduced pressure, and the residue was applied to flash column chromatography on silica gel using a mixture of methylene chloride and methanol in the ratio 23:2, as eluant. Product was obtained as a white solid, 276.6 mg, (99%). IR (KBr): 3500–2800; 1700; 1550; 1500; 1300; 1100; 800 cm$^{-1}$. $^1$H-NMR (DMSO; δ in ppm): 1.70 (s, 6H; 2×CH$_3$); 2.10 (s, 3H; CH$_3$); 2.10–2.40 (m, 4H; H-2'+H-2"); 3.40–370 (m, 2H; H-4'+H-4"); 3.80 (bs, 1H; OH); 4.00–4.30 (m, 4H; H-5'+H-5"); 5.10–5.30 (m, 2H; H-3'+H-3"); 6.10–6.30 (m, 2H; H-1'+H-1"); 7.50 and 7.80 (2s, 2H; 2×H-6); 7.90 (bs, H; NH); 11.30 and 11.40 (2s, 2H; 2×NH).

The next step was synthesis of 5'-O-Dimethoxytrityl-3'-amino-3'-deoxythymidylyl-(3'-5'-carbamoyl)-3'-O-acetyl-deoxythymidine, 3. 3'-Amino-3'-deoxythymidylyl-(3'-5'-carbamoyl)-3'-O-acetyl-deoxythymidine, (1, 203.5 mg; 0.366 mmole), and 4,4'-dimethoxytrityl chloride (186.02 mg; 0.55 mmole) were dissolved in 5 ml of anhydrous pyridine at room temperature. The reaction mixture was left overnight with stirring under a nitrogen atmosphere. The resultant suspension was then poured into water containing ice and the product was extracted with methylene chloride (3×50 ml). The combined extracts were washed with water (3×50 ml), dried over anhydrous sodium sulfate, filtered, and evaporated to dryness in vacuo. The residual solid was applied to flash column chromatography on silica gel using a mixture of methylene chloride, methanol, and triethylamine in the ratio 23:1:1, as eluant. Product was obtained as a white solid, 309 mg, (98%). IR (KBr): 3500–2800; 1700; 1600; 1500; 1300; 1150; 1000; 950; 850; 790; 750; 550 cm$^{-1}$. $^1$H-NMR (DMSO; δ in ppm); 1.78 and 1.80 (2s; 6H; 2×CH$_3$); 2.10 (s, 3H; CH$_3$); 2.30–2.50 (m, 4H; H-2'+H-2"); 3.30–3.60 (m, 2H; H-4'+H-4"); 3.75 (s, 6H; 2×OCH$_3$); 3.90–4.10 (m, 2H; H-5'); 4.30–4.50 (m, 2H; H-5"); 5.40 (m, H; H-3'); 6.0 (m, H; H-3"); 6.30–6.40 (m, 2H; H-1'+H-1"); 6.80–6.90 (m, phenyls); 7.20–7.30 (m, phenyls); 7.40 (bs, 2H; H-6); 7.60 (bs; 1H; NH); 10.30 (bs, 2H; 2×NH).

The 5'-protected dimeric building block 5'-O-dimethoxytrityl-3'-amino-3'-deoxythymidylyl-(3'-5'-carbamoyl) deoxythymidine, 4, was then prepared as follows. 5'-O-Dimethoxytrityl-3'-amino-3'-deoxythymidylyl-(3'-5'-carbamoyl)-3'-O-acetyl-deoxythymidine, 3, (309 mg) was dissolved in 5 ml of conc. ammonia and stirred for 3 hours at room temperature. After the removal of ammonia in vacuo, the residual solid was applied to flash column chromatography on silica gel and eluted with a mixture of methylene chloride, methanol, and triethylamine in the ratio 22:2:1, to yield 290 mg (98%) product as white solid. IR (KBr): 3500–2800, 1750; 1500; 1450; 1300; 1200; 1100–1000; 900; 700; 600 cm$^{-1}$. $^1$H-NMR (CDCl$_3$; δ in ppm): 1.35 and 1.80 (2s, 6H; 2×CH$_3$); 2.0 (s, 2H; H-2'); 2.40 (bs, H; OH); 2.70 (s, 2H; H-2"); 3.25–3.50 (m, 2H; H-4'+H-4"); 3.75 (s, 6H; OCH$_3$); 4.0–4.30 (m, 2H, H-5'); 4.30–4.50 (m, 2H; H-5"); 5.90–6.0 (m, 2H, H-3'+H-3"); 6.20–6.40 (m, 2H; H-1'+H-1"); 6.70–6.90 (m, phenyls); 7:15–7.30 (m, phenyls); 7.40 (bs, 2H; H-6); 7.60 (bs, H; NH).

The dimeric building block was then either converted to a trimeric building block or converted to its 3'-phosphoramidite in the dimer form. For trimer synthesis, the dimer was first activated at the 5' position with (bis-p-nitrophenyl)carbonate, see FIG. 1, to give 5'-carbonate which was further reacted with 3'-amino-3'-deoxythymidine. Thus obtained trimer was then protected at the 5' position to give 5'-ODMT-protected trimer, followed by hydrolysis in ammonia to generate free 3'-hydroxyl. Product, 5, was obtained as a white powder in 78.4% yield. IR (KBr): 3500–2800; 1750; 1500; 1460; 1250; 1180; 1150–1050; 850; 800 cm$^{-1}$. $^1$H-NMR (DMSO; δ in ppm): 1.50, 1.70, and 1.80 (3s, 9H; 3×CH$_3$); 1.75 (bs, H; OH); 2.10–2.50 (m, 6H; H-2'+H-2"+H-2'''); 3.10–3.40 (m, 3H; H-4'+H-4"+H-4'''); 3.75 (s, 6H; 2×OCH$_3$) 3.90–4.40 (m, 6H; H-5'+H-5"+H-5'''); 6.10–6.30 (m, 3H; H-3'+H-3"+H-3'''); 6.80–6.90 (m, phenyls); 7.20–7.40 (m, phenyls, and 3H; H-1'+H-1"+H-1'''); 7.40–7.60 (m, 3H; H-6); 7.80–8.0 (m, 2H; 2×NH), 11.40 (m, 3H; 3×NH).

Conversion of the trimer to a tetramer was carried out by again repeating these steps. Product, 6, was obtained as a white powder in 83.8% yield. IR (KBr): 3600–2800; 1750; 1500; 1490; 1350; 1200; 1100–1000; 800; 750 cm$^{-1}$. $^1$H-NMR (DMSO; δ in ppm): 1.50, 1.70, 1.80, and 1.90 (4s, 12H; 4×CH$_3$); 1.60 (bs, H; OH); 2.00–2.50 (m, 8H; H-2'+H-2"+H-2'''+H-2''''); 3.0–3.40 (m, 4H; H-4'+H-4"+H-4'''+H-4''''); 3.70 (s, 6H; 2×OCH$_3$); 3.80–4.40 (m, 8H; H-5'+H-5"+H-5'''+H-5''''); 6.10–6.30 (m, 4H; H-4'+H-4"+H-4'''+H-4''''); 6.80–7.0 (m, phenyls); 7.20–7.40 (m, phenyls; and 4H; H-6); 7.80–8.0 (m, 3H; 3×NH); 11.30–14.40 (m, 4H; 4×NH).

Dimers were converted to their corresponding β-cyanoethylphosphoramidites by the following chemistry. The 5'-O-DMT protected dimer, 4, trimer, 5, or tetramer, 6, was dried over P$_2$O$_5$ at 70° C. for 24 hours in vacuo and co-evaporated with anhydrous benzene and anhydrous methylene chloride, (3×mixture of 2 ml methylene chloride and 5 ml benzene), dissolved in dry methylene chloride (2 ml). Triethylamine (1 ml) was added to the solution, followed by addition of (N,N-diisopropylamino)(2-cyanoethoxy)chlorophosphine, (173.96 mg, 0.735 mmole). The reaction was stirred for 60 minutes under nitrogen. The reaction mixture was poured into a cold saturated aqueous solution of sodium bicarbonate and the product was extracted with methylene chloride (3×20 ml). The combined organic extracts were washed with brine (3×10 ml), dried over anhydrous sodium sulfate, filtered and then evaporated to dryness in vacuo. The residual solid was dissolved in methylene chloride (2 ml) and precipitated with hexane (600 ml) containing N,N-diisopropylethylamine (2 ml) at −78° C. The white precipitate was filtered off, collected and dried invacuo over P$_2$O$_5$, to give, for the dimer building block, 182 mg, (73%), white solid which was directly used in the synthesis of oligonucleotides. $^{31}$P-NMR (CDCl$_3$; δ in ppm); 144.65 and 144.20. It is possible to generate phosphoramidites of trimers and tetramers in the same way. Due to a steric hindrance, reduced yields and coupling efficiencies in the automated DNA synthesis will be expected for these.

For each of the above product analyses, $^1$H- and $^{31}$P-NMR spectra were measured with a Varian Unity 300 spectrometer using TMS as the internal standard and 85% H$_3$PO$_4$ as the external standard. The IR spectra were recorded on a Nicolet 800 spectrometer using samples as KBr disks.

EXAMPLE 2

Synthesis of Oligonucleotides Containing Novel Carbamate Internucleoside Linkages at Various Positions To synthesize oligonucleotides having 1, 2, or 3 novel carbamate internucleoside linkages at the most 3' positions, 5'-protected dimeric, 4, trimeric, 5, or tetrameric, 6, building blocks were attached onto long chain alkylamidopropanoic acid controlled pore glass (CPG) beads, since the carboxyl moiety could be esterified directly with 3'-hydroxyl group of dimer 4, trimer, 5, or tetramer, 6 in the presence of 1-(3-dimethylaminopropryl)-3-ethylcarbodiimide hydrochloride, using standard procedures (see, e.g., Damha et al, Nucleic Acids Res. 18:3813 (1990)). Initial loadings were found to be 37.4, 27.5 and 2.2 μmole/g CPG for dimeric, 4, trimeric, 5, and tetrameric, 6, building blocks respectively. To improve the loading values for the trimeric and tetrameric building blocks, they were first succinilated at the 3'-OH position and then attached to long chain alkylamino controlled pore glass support via an amide bond, using standard procedures (see, e.g., Caruthers et al., Methods In Enzymology 154:287 (1987); Damha et al., Nucleic Acids Res. 18:3813 (1990)). This manipulation modified loading values to 25.0 and 14.6 μmole/g CPG for the trimeric, 5, and tetrameric, 6, building blocks, respectively.

Approximately 10 mg of CPG-bound dimethoxytrityl di-, tri- or tetra-nucleoside carbamate was placed into a 10 ml volumetric flask and treated with 0.2 ml HClO$_4$-ethanol (3:2) for 1 minute to release the dimethoxytrityl groups. Then 9.8 ml acetonitrile was added and absorbance of light at 498 mm was measured to determined loading efficiency according to the equation:

$$\frac{A_{498} \times 10 \times 14.3}{\text{weight CPG (mg)}} = \mu\text{mole/g}$$

For oligonucleotides having one, two, or three internucleoside linkages exclusively at the most 3'-position(s), the CPG bound dimer, trimer, or tetramer, respectively, was used for initiating synthesis of the oligonucleotide. Synthesis was carried out according to standard procedures, using monomeric nucleoside cyanoethylphosphoramidites except that in certain cycles, monomers were replaced with dinucleoside carbamate cyanoethylphosphoramidites according to the invention. Using this procedure, oligonucleotides having novel carbamate internucleoside linkage at various positions were assembled, as shown in Table II, below.

TABLE II

OLIGONUCLEOTIDES CONTAINING NOVEL CARBAMATE INTERNUCLEOSIDE LINKAGES AT VARIOUS POSITIONS

| | | |
|---|---|---|
| SEQ ID NO:1 | 5'-CTCGCACCCATCTCTCTCCT*T-3'; | PO |
| SEQ ID NO:2 | 5'-CTCTCGCACCCATCTCTCTCCT*T*T-3'; | PO |
| SEQ ID NO:3 | 5'-CTCTCGCACCCATCTCTCTCCT*T*T-3'; | PO |
| SEQ ID NO:4 | 5'-CTCGCACCCATCTCTCTCCT*TT*TT*T-3'; | PO |
| SEQ ID NO:5 | 5'-T*TCTCGCACCCT*TT*TATCTCTCTCCT*T-3'; | PO |
| SEQ ID NO:6 | 5'-T*TGT*TCT*TCT*TGT*TGT*TCT*TCT*T*T-3'; | PO |
| SEQ ID NO:7 | 5'-CTCTCGCACCCATCTCTCTCCT*T*T*-3'; | PS |

PO = phosphodiester
PS = phosphorothioate
*= 5'-deoxythymidyl-3'-NH—CO—O—5'-deoxythymidyl-3'

Oligonucleotides were cleaved off the CPG and deprotected with concentrated ammonium hydroxide at room temperature for one hour, then at 55° C. for five hours. The resultant 5'-O-DMT-protected oligonucleotides were purified on a preparative C-18 reverse phase column by elution with a linear gradient of solvent A (0.1 M aqueous ammonium acetate) and solvent B (20% 0.1 M ammonium acetate+80% acetonitrile). The oligonucleotides were detritylated in 80% aqueous acetic acid for 30 minutes at room temperature, then purified again by repeating the C-18 chromatography step.

EXAMPLE 3

Assessment Of Nuclease Resistance of Oligonucleotides Having Novel Carbamate Internucleoside Linkages at Various Positions Each of the oligonucleotides shown in Table II was tested for its ability to resist exonucleolytic digestion. 0.2 O.D. units oligonucleotide was dissolved in 0.5 ml 10 mM Tris (pH 8.5), 10 mM $MgCl_2$ containing 5 µl/ml snake venom phosphodiesterase I (type VIII S from *Crotulus atrox*, Sigma, St. Louis, Mo.) and incubated at 37° C. Digestion was measured by monitoring absorbance of UV light at 260 nm. The results for each oligonucleotide are shown in Table III, below.

TABLE III

EXONUCLEOLYTIC DIGESTION OF OLIGONUCLEOTIDES

| Oligonucleotide | $t_{1/2}$ (minutes) |
| --- | --- |
| All PO 27-mer | 1.25 |
| SEQ. ID. NO.: 1 | 3.70 |
| SEQ. ID. NO.: 2 | 5.85 |
| SEQ. ID. NO.: 3 | 5.80 |
| SEQ. ID. NO.: 4 | 2.15 |
| SEQ. ID. NO.: 5 | 4.05 |
| SEQ. ID. NO.: 6 | 3.33 |
| SEQ. ID. NO.: 7 | >>30 |

These results demonstrate that oligonucleotides containing novel carbamate internucleoside linkages are more resistant to exonucleolytic digestion than oligonucleotides containing only phosphodiester internucleoside linkages. The stability increased with increasing numbers of 3' carbamate linkages, provided that such linkages were consecutive and not interspersed with phosphodiester linkages. Oligonucleotides having 3' carbamate linkages and the remainder phosphorothioate linkages were especially stable, with no discernable degradation after 30 minutes digestion.

EXAMPLE 4

Binding Properties of Oligonucleotides Having Novel Carbamate Internucleoside Linkages at Various Positions Each of the oligonucleotides shown in Table II was tested for its binding properties for a complementary oligonucleotide phosphodiester. For each oligonucleotide, 0.2 O.D. units of oligo and 0.2 O.D. units of its complement were dissolved in 1 ml 10 mM $Na_2HPO_4$ (pH 7.4), 100 mM NaCl in a closed system cuvette having a thermal range of 25° C. to 80° C. (Lambda 2™ spectrophotometer, Perkin Elmer, Uberlingen, Germany). Temperature within the range was raised at a rate of 1° C./minute and increase in $A_{260}$ was measured. The results for each oligonucleotide are shown in Table IV, below.

TABLE IV

BINDING PROPERTIES OF OLIGONUCLEOTIDES

| Oligonucleotide | $T_m$ (carbamate ° C.) | $T_m$ (° C., all PO analog) |
| --- | --- | --- |
| SEQ ID NO: 1 | 63.3 | 63.8 |
| SEQ ID NO: 2 | 67.5 | 67.7 |
| SEQ ID NO: 3 | 67.4 | 67.7 |
| SEQ ID NO: 4 | 65.3 | 66.5 |
| SEQ ID NO: 5 | 58.6 | 65.5 |
| SEQ ID NO: 6 | 16.9 | 56.2 |
| SEQ ID NO: 7 | 59.8 | 60.1[2] |
| SEQ ID NO: 8[1] | — | 67.9 |
| SEQ ID NO: 3[3] | 65.0 | 65.0 |
| SEQ ID NO: 8[3] | — | 62.9 |
| SEQ ID NO: 3[4] | 61.9 | 61.9 |
| SEQ ID NO: 8[4] | — | 59.9 |

[1]5'-CTCTCGCACCCATCTCTCTCCCCCC-3', all PO; sequence is identical to SEQ ID NO: 3, except that the last 4 nucleotides are changed to C, thus making a 4 b.p. mismatch with its duplex partner.
[2]All phosphorothioate analog.
[3]Second experiment carried out in 5 mM $Na_2HPO_4$ (pH 7.4), 50 mM NaCl.
[4]Third experiment carried out in 2.5 mM $Na_2HPO_4$ (pH 7.4), 25 mM NaCl.

These results support at least two conclusions. First, the introduction of one, two, or three novel carbamate linkages into the most 3' positions of an oligonucleotide has little or no effect on its ability to bind to a complementary nucleic acid. In contrast, the introduction of three novel carbamate linkages at more interior sites results in a modest inhibitory effect, and the introduction of additional novel carbamate linkages throughout the oligonucleotide causes a dramatic reduction in binding. Thus, oligonucleotides having three or fewer novel carbamate linkages at the most 3' positions are likely to be the best candidates as antisense agents.

Second, when three or fewer novel carbamate linkages are present near the 3' end of an oligonucleotide, these linkages do not significantly interfere with base stacking involving the adjacent nucleosides. This is demonstrated by comparing the stability of oligonucleotide duplexes having 3' mismatches (and thus lacking the ability to undergo terminal base stacking) with that of an oligonucleotide duplex having three 3' terminal novel carbamate linkages. At high ionic strengths, under which duplex formation is stabilized, the two behave similarly $T_m$s of 67.9° C. and 67.4° C., respectively). However, as ionic strength is reduced, thus favoring duplex dissociation, the latter oligonucleotide becomes more stable ($T_m$s of 62.9° C. v. 65.0° C. respectively at 50 mM salt and 59.9° C. v. 61.9° C. respectively at 25 mM salt). These results indicate that terminal base pairing and base stacking occur in the novel carbamate-containing oligonucleotide, thus stabilizing its duplex with an oligonucleotide phosphodiester, relative to a duplex having terminal mismatches.

What is claimed is:

1. A dinucleoside carbamate whose structure is 5'-nucleoside-3'-NHCOO-5'-nucleoside-3', wherein the nucleoside at the first occurrence is 3'-deoxythymidinyl and the nucleoside at the second occurrence is 5'-deoxythymidinyl.

2. A trinucleoside carbamate with one or two carbamate linkages, which carbamate linkages are oriented in the same way as the dinucleoside carbamate according to claim 1, and wherein the other linkages are independently any other non-carbamate internucleoside linkage; and wherein the nucleosides coupled by a carbamate linkage are at the first occurrence a 3'-deoxythymidinyl and at the second occurrence a 5'-deoxythymidinyl.

3. A method of synthesizing an oligonucleotide with one or more carbamate linkages comprising covalently linking a trinucleoside carbamate to a growing nascent oligonucleotide chain undergoing chemical synthesis, the trinucleoside carbamate being a trinucleoside carbamate according to claim 2.

4. A method of synthesizing an oligonucleotide with one or more carbamate linkages comprising covalently linking one or more nucleotides to a trinucleoside carbamate that has been covalently linked to a solid support suitable for oligonucleotide synthesis, the trinucleoside carbamate being a trinucleoside carbamate according to claim 2.

5. A tetranucleoside carbamate with one, two, or three carbamate linkages, which carbamate linkages are oriented in the same way as the dinucleoside carbamate according to claim 1, and wherein the other linkages are independently any other non-carbamate internucleoside linkage; and wherein the nucleosides coupled by a carbamate linkage are at the first occurrence a 3'-deoxythymidinyl and at the second occurrence a 5'-deoxythymidinyl.

6. A method of synthesizing an oligonucleotide with one or more carbamate linkages comprising covalently linking one or more nucleotides to a tetranucleoside carbamate that has been covalently linked to a solid support suitable for oligonucleotide synthesis, the tetranucleoside carbamate being a tetranucleoside carbamate according to claim 5.

7. A method of synthesizing an oligonucleotide with one or more carbamate linkages comprising covalently linking a tetranucleoside carbamate to a growing nascent oligonucleotide chain undergoing chemical synthesis, the tetranucleoside carbamate being a tetranucleoside carbamate according to claim 5.

8. A method of synthesizing an oligonucleotide with one or more carbamate linkages comprising covalently linking one or more nucleotides to a dinucleoside carbamate that has been covalently linked to a solid support suitable for oligonucleotide synthesis, the dinucleoside carbamate being a dinucleoside carbamate according to claim 1.

9. A method of synthesizing an oligonucleotide with one or more carbamate linkages comprising covalently linking a dinucleoside carbamate to a growing nascent oligonucleotide chain undergoing chemical synthesis, the dinucleoside carbamate being a dinucleoside carbamate according to claim 1.

10. An oligonucleotide of from about 8 to about 100 nucleotides in length with from one to all internucleoside linkages being carbamate linkages, the carbamate linkages being oriented in the same way as the dinucleoside carbamate linkage according to claim 1, and wherein the nucleosides coupled by a carbamate linkage are at the first occurrence a 3'-deoxythymidinyl and at the second occurrence a 5'-deoxythymidinyl.

11. The oligonucleotide according to claim 10, wherein the carbamate internucleoside linkage(s) are at one or more of the three most 3' internucleoside positions in the oligonucleotide.

12. The oligonucleotide according to claim 11, wherein from one to all of the non-carbamate internucleoside linkages are phosphorothioate linkages, which may be located at any non-carbamate internucleoside position, and the other non-carbamate, non-phosphorothioate linkages are any other type of internucleoside linkage.

13. The oligonucleotide according to claim 11, wherein from one to all of the non-carbamate internucleoside linkages are phosphodiester linkages, which may be located at any non-carbamate internucleoside position, and the other non-carbamate, non-phosphorothioate linkages are any other type of internucleoside linkage.

* * * * *

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1:

CTCGCACCCA TCTCTCTCCT T                                              21

(2) INFORMATION FOR SEQ ID NO: 2:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 2:

CTCTCGCACC CATCTCTCTC CTTT                                           24

(2) INFORMATION FOR SEQ ID NO: 3:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 3:

CTCTCGCACC CATCTCTCTC CTTTT                                          25

(2) INFORMATION FOR SEQ ID NO: 4:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 4:

CTCGCACCCA TCTCTCTCCT TTTTT                              25

(2) INFORMATION FOR SEQ ID NO: 5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 5:

TTCTCGCACC CTTTTATCTC TCTCCTT                            27

(2) INFORMATION FOR SEQ ID NO: 6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 6:

TTGTTCTTCT TGTTGTTCTT CTTTT                              25

(2) INFORMATION FOR SEQ ID NO: 7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 7:

CTCTCGCACC CATCTCTCTC CTTTT                              25

(2) INFORMATION FOR SEQ ID NO: 8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 8:

CTCTCGCACC CATCTCTCTC CCCCC                              25